United States Patent
Carmi

(10) Patent No.: US 10,032,268 B2
(45) Date of Patent: Jul. 24, 2018

(54) DYNAMIC CONTRAST-ENHANCED IMAGING BASED PERMEABILITY METRIC

(71) Applicant: KONINKLIJKE PHILIPS N.V., Eindhoven (NL)

(72) Inventor: Raz Carmi, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 315 days.

(21) Appl. No.: 14/417,569

(22) PCT Filed: Jul. 12, 2013

(86) PCT No.: PCT/IB2013/055735
§ 371 (c)(1),
(2) Date: Jan. 27, 2015

(87) PCT Pub. No.: WO2014/024061
PCT Pub. Date: Feb. 13, 2014

(65) Prior Publication Data
US 2015/0221082 A1 Aug. 6, 2015

Related U.S. Application Data
(60) Provisional application No. 61/679,918, filed on Aug. 6, 2012.

(51) Int. Cl.
*G06T 7/00* (2017.01)
*G06K 9/52* (2006.01)
(Continued)

(52) U.S. Cl.
CPC ........ *G06T 7/0012* (2013.01); *A61B 5/02028* (2013.01); *A61B 5/055* (2013.01);
(Continued)

(58) Field of Classification Search
None
See application file for complete search history.

(56) References Cited

U.S. PATENT DOCUMENTS 6,891,918 B2 * 5/2005 Drummond ............ A61B 6/032
378/5
2002/0026116 A1 2/2002 Schmainda
(Continued)

FOREIGN PATENT DOCUMENTS

FR 2913874 A1 9/2008
WO 2011095898 A1 8/2011

OTHER PUBLICATIONS

Daldrup et al. "Correlation of Dynamic Contrast-Enhanced MR Imaging with Histologic Tumor Grade: Comparison of Macromolecular and Small-Molecular Contrast Media," AJR Am J Roentgenol. Oct. 1998;171(4):941-9.*

(Continued)

*Primary Examiner* — Matthew Bella
*Assistant Examiner* — Soo Shin

(57) ABSTRACT

A method includes determining a permeability metric of vascular tissue of interest based on a first time enhancement curve and second time enhancement curve corresponding to a first contrast material and a second contrast material flowing through the vascular tissue of interest and generating a signal indicative thereof. A computing system includes a time enhancement curve generator (114) that receives first dynamic contrast enhanced imaging data representing vascular tissue of interest and a first contrast material with weakly permeating particles and that receives second dynamic contrast enhanced imaging data representing the vascular tissue of interest and a second contrast material with strongly permeating particle, and generates a first time enhancement curve for the first contrast material and a second time enhancement curve for the second contrast (Continued)

material, and a permeability metric determiner (116) that determines a permeability metric for the vascular tissue of interest by determining an effective difference between the first and second time enhancement curves.

22 Claims, 5 Drawing Sheets

(51) Int. Cl.
  G01R 33/563 (2006.01)
  G01R 33/56 (2006.01)
  A61B 8/08 (2006.01)
  A61B 5/055 (2006.01)
  A61B 5/02 (2006.01)
  A61B 6/00 (2006.01)
  A61B 6/03 (2006.01)
(52) U.S. Cl.
  CPC .............. A61B 6/481 (2013.01); A61B 6/507 (2013.01); A61B 6/5217 (2013.01); A61B 8/481 (2013.01); A61B 8/5223 (2013.01); G01R 33/5601 (2013.01); G01R 33/56366 (2013.01); G06K 9/52 (2013.01); A61B 6/037 (2013.01); A61B 6/4258 (2013.01); A61B 6/583 (2013.01)

(56) References Cited

U.S. PATENT DOCUMENTS

| | | | |
|---|---|---|---|
| 2004/0024317 A1* | 2/2004 | Uzgiris | A61K 49/0004 600/458 |
| 2004/0101969 A1* | 5/2004 | Viglianti | A61B 5/055 436/173 |
| 2004/0242994 A1 | 12/2004 | Brady et al. | |
| 2005/0228269 A1 | 10/2005 | Ashton | |
| 2009/0130023 A1 | 5/2009 | Dahnke et al. | |
| 2010/0030073 A1* | 2/2010 | Kalafut | A61B 6/481 600/431 |
| 2010/0296714 A1 | 11/2010 | Schmainda et al. | |
| 2011/0150309 A1 | 6/2011 | Barfett et al. | |
| 2011/0243847 A1 | 10/2011 | Wiebelitz | |
| 2011/0257519 A1 | 10/2011 | Bj?rnerud et al. | |
| 2011/0274333 A1* | 11/2011 | Prevrhal | G06T 11/005 382/132 |
| 2012/0314925 A1 | 12/2012 | Peligrad | |

OTHER PUBLICATIONS

Lee et al. "PET/MRI Dual-Modality Tumor Imaging Using Arginine-Glycine-Aspartic (RGD)-conjugated Radiolabeled Iron Oxide Nanoparticles," J Nucl Med. Aug. 2008;49(8):1371-9.*
Tang et al. "Improving Penetration in Tumors with Nanoassemblies of Phospholipids and Doxorubicin," JNCI, vol. 99, No. 13, Jul. 4, 2007.*
Henderson et al. "Simultaneous MRI Measurement of Blood Flow, Blood Volume, and Capillary Permeability in Mammary Tumors Using Two Different Contrast Agents," Journal of Magnetic Resonance Imaging, 12: 991-1003 (2000).*
Xu et al. "Evaluation of Hepatocellular Carcinoma by Contrast-Enhanced Sonography," J Ultrasound Med, 2011; 30: 625-633.*
Plassat et al., "Sterically stabilized superparamagnetic liposomes for MR imaging and cancer therapy: Pharmacokinetics and biodistribution," Int J Pharm. Nov. 1, 2007;344(1-2):118-27. Epub May 17, 2007.*
Daldrup, H., et al.; Correlation of Dynamic Contrast-Enhanced MR Imaging with Histologic Tumor Grade: Comparison of Macromolecular and Small-Molecular Contrast Media; 1998; AJR; 171:941-949.
Henderson, E., et al.; Simultaneous MRI measurement of blood flow, blood volume, and capillary permeability in mammary tumors using two different contrast agents; 2000; Journal of Magnetic Resonance Imaging; 12(6)991-1003.
Miles, K. A., et al.; Perfusion CT: a worthwhile enhancement?; 2003; The British Journal of Radiology; 76:220-231.
Miles, K. A., et al.; CT measurements of capillary permeability within nodal masses: a potential technique for assessing the activity of lymphoma; 1997; The British Journal of Radiology; 70:74-79.
Peer, D., et al.; Nanocarriers as an emerging platform for cancer therapy; 2007; Nature Nanotechnology; vol. 2; 751-760.
Sourbron, S. P., et al.; Tracer kinetic modelling in MRI: estimating perfusion and capillary permeability; 2012; Phys. Med. Biol.; 57:R1-R33.

* cited by examiner

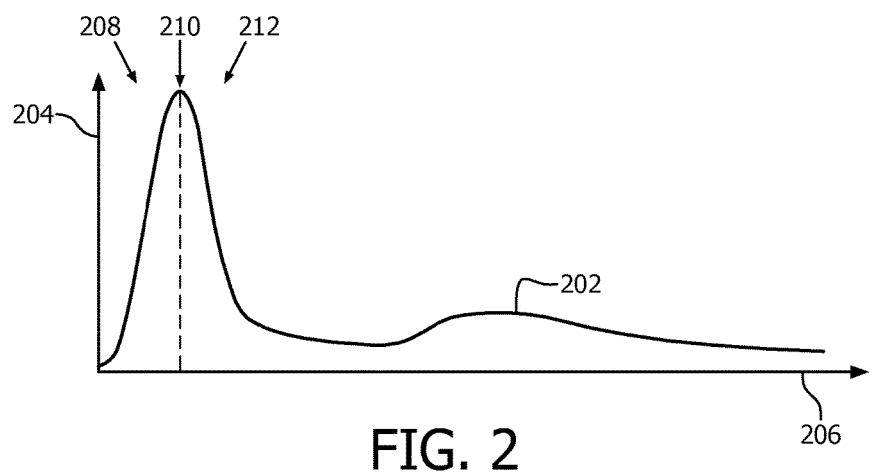
FIG. 2
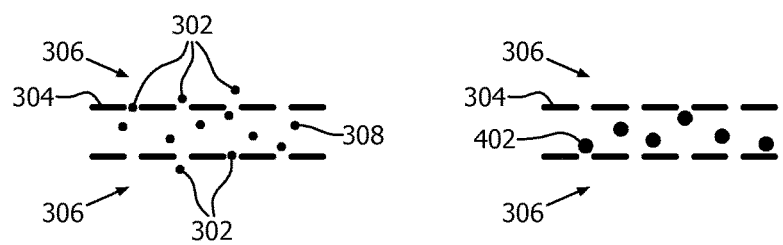
FIG. 3
FIG. 4
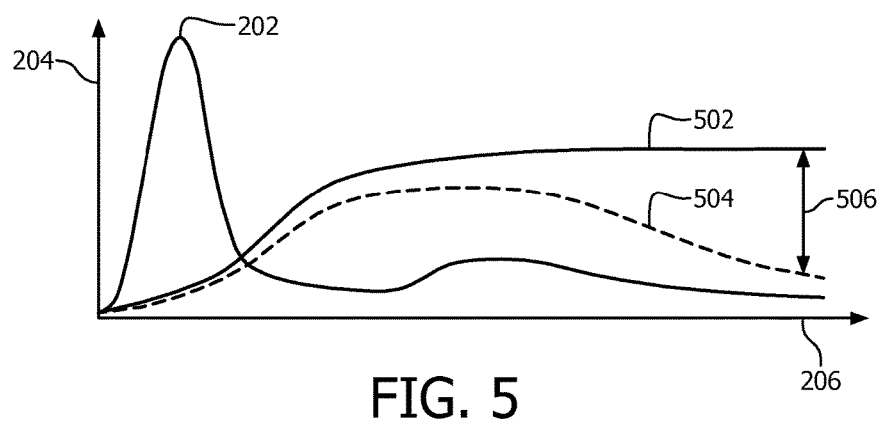
FIG. 5

DYNAMIC CONTRAST-ENHANCED IMAGING BASED PERMEABILITY METRIC

CROSS REFERENCE TO RELATED APPLICATIONS

This application is a national filing of PCT application Ser. No. PCT/IB2013/055735, filed Jul. 12, 2013, published as WO 2014/024061 A1 on Feb. 13, 2014, which claims the benefit of U.S., Provisional Application Ser. no. 61/679,918 filed Aug. 6, 2012, which is incorporated herein by reference.

The following generally relates to dynamic contrast-enhanced imaging and more particularly to determining a tissue permeability metric based on imaging data from a dynamic contrast-enhanced scan performed with a computed tomography (CT), magnetic resonance (MR), positron emission tomography (PET), single photon emission tomography (SPECT), hybrid or combined CT/MR, CT/PET, CT/SPECT, PET/MR, etc. and/or other imaging modality.

Tumor vascular permeability, in which blood penetrates from the capillaries into the interstitial space, is caused by tumor blood vessels which have defective and leaky endothelium. Several physiological processes that occur in rapidly growing tumors lead to the development of neoangiogenic vessels, which are immature and tortuous and have increased permeability to macromolecules due to large endothelial cell gaps, incomplete basement membrane, and absence of smooth muscles. These abnormal tumor vessels can be used as potential markers to assess the tumor grade. Thus, in-vivo measurement of tumor vessel permeability is important for several reasons: 1) it can be used for grading tumors since increased permeability is associated with immature blood vessels, which are seen with neoangiogenesis; 2) it can be used to study the response of tumors to various therapies, especially antiangiogenic therapy; 3) understanding the concept of permeability can help in understanding the mechanism of the entry of therapeutic agents into target cells, and hence to improve drug delivery.

In medical diagnostics, permeability can be measured in principle by dynamic contrast-enhanced (DCE) imaging in addition to the more conventional blood perfusion assessment. Perfusion imaging is particularly useful for studying patients with brain, heart, lungs, kidneys or liver damage, e.g. as a result of stroke, infract, tumors etc. and general functionality of the body organs with respect to many organ specific diseases. Since perfusion and permeability imaging basically measures blood flow characteristics, several imaging modalities can be used with the appropriate administered contrast materials. For example, perfusion imaging can be performed by CT using iodine contrast agent, MRI with gadolinium or iron-oxide contrast agent, PET and SPECT with several types of radiotracers, and ultrasound with micro-bubbles contrast agents. In animal preclinical imaging, optical tomography with fluorescent agents is applicable as well.

DCE imaging usually requires repeated imaging of the volume of interest for a number of different time points, for example, between 3-30 repeated scans with a few seconds difference between successive scans (e.g. 1 to 10 sec per time frame). In common DCE techniques, a bolus of a contrast agent is administered into the patient's vascular system, for example by an automatic injector, and images from the region of interest are collected for a period covering the transit of the contrast agent bolus through the tissue in the region of interest. The local concentration changes of the contrast agent (as can be inferred from image data) along time are used for analyzing physiological parameters. In clinical practice, it is common for the DCE image series to be inspected qualitatively or to be assessed quantitatively with special analysis algorithms. A quantified result may include, for a region or per voxel, an absolute measurement of blood flow or perfusion, blood volume, mean transit time, time of arrival, permeability, time to peak, peak intensity, maximal gradient and other parameters.

Permeability assessment has mainly been studied in brain perfusion where the brain blood barrier increases the difference between normal to damaged tissues. However, measuring tumor permeability in other body tissue types is much more difficult and improved techniques are required. The current techniques for assessing tumor capillary permeability in all relevant imaging modalities are based on analyzing the time enhancement curve of a contrast agent during dynamic contrast-enhanced imaging. From the measured data, both perfusion parameters and permeability parameters can be calculated in principle. However, since both effects are combined together within the data, a relatively large set of accurate measurements are required to enabling sensitive analysis such as the Patlak-plot or other similar models which can separate between the two influences. The Patlak-plot analysis uses a two compartmental model (blood and tissue extra cellular fluid, ECF) of the dynamic data.

For the Patlak-plot analysis, consider the one-way transfer of contrast medium from the blood to the ECF with a blood clearance value of contrast α. The amount of contrast medium that has left the blood will be equal to: alpha times the amount of blood that has flowed through the tissue. The concentration of contrast medium or the enhancement of the ECF will be (α/V) (AUC) of the blood curve, where V is the volume of the tissue and AUC is the area under the input (artery) curve. The enhancement of the tissue due to blood in the tissue is determined by the relative blood-volume to tissue-volume (rBV) multiplied by the concentration of contrast medium in the blood. Thus, the total concentration of contrast medium, i.e. enhancement of the tissue at time t is given by the sum of the concentrations of the contrast medium in the blood and ECF as shown in EQUATION 1:

$$c(t) = rBV \cdot b(t) + \frac{\alpha}{V} \int_0^t b(t') dt', \qquad \text{EQUATION 1}$$

where c(t) is the concentration in the tissue and b(t) is the concentration in the input artery.

In order to find the permeability coefficient α/V, a plot of the ratio of the tissue to blood concentration against the ratio of the AUC(t) of the blood curve to the blood concentration for various time values has an intercept of the tissue's relative blood volume (rBV) and a slope equal to the blood clearance per unit volume or permeability (α/V). The literature has indicated that typical measured permeability values are in a range of up to 0.5-5.0 [1/min/100] for normal tissues, and up to the range of 10.0-30.0 [1/min/100] for cancerous tissues.

Unfortunately, the Patlak-plot analysis model is susceptible to inaccuracy. A source of the inaccuracy is the fact that two unknown values—rBV and α/V—are determined: As consequence, a relatively long sampling time range and several different sampled points are required in order to reduce the degeneracy of the solved equation set (i.e. to obtain a stable unique solution). Therefore, there is an unresolved need for other approaches for determining permeability based on imaging data.

Aspects described herein address the above-referenced problems and others.

In one aspect, a method includes determining a permeability metric of vascular tissue of interest based on a first time enhancement curve and second time enhancement curve corresponding to a first contrast material and a second contrast material flowing through the vascular tissue of interest and generating a signal indicative thereof.

In another aspect, a computing system includes a time enhancement curve generator that receives first dynamic contrast enhanced imaging data representing vascular tissue of interest and a first contrast material with weakly permeating particles and that receives second dynamic contrast enhanced imaging data representing the vascular tissue of interest and a second contrast material with strongly permeating particle, and generates a first time enhancement curve for the first contrast material and a second time enhancement curve for the second contrast material, and a permeability metric determiner that determines a permeability metric for the vascular tissue of interest by determining an effective difference between the first and second time enhancement curves.

In another aspect, computer readable storage medium encoded with one or more computer executable instructions, which, when executed by a processor of a computing system, causes the processor to: determine a permeability metric of vascular tissue of interest based a first time enhancement curve and second time enhancement curve corresponding to a first contrast material and a second contrast material flowing through the vascular tissue of interest, and visually displaying at least one of the permeability metric or the first or second time enhancement curves.

The invention may take form in various components and arrangements of components, and in various steps and arrangements of steps. The drawings are only for purposes of illustrating the preferred embodiments and are not to be construed as limiting the invention.

FIG. 1 schematically illustrates a computing system configured to determine a permeability of vascular tissue of interest and a plurality of imaging scanners.

FIG. 2 illustrates a prior art time enhance curve for an artery.

FIG. 3 illustrates strongly-permeating contrast material molecules in connection with a tumor.

FIG. 4 illustrates weakly-permeating contrast material molecules in connection with a tumor.

FIG. 5 illustrates time enhance curves for the strongly-permeating contrast material and the weakly-permeating contrast material.

The following describes an approach for assessing vascular tissue (e.g., tumor) permeability based on dynamic contrast-enhanced (perfusion) imaging using at least two different contrast materials, one with more weakly permeating particles and one with more strongly permeating particles. Such scans involve administration of a contrast material(s) and scans over time to capture contrast agent uptake and washout. As described in greater detail below, the time enhancements curve for both contrast materials are generated and used to determine the permeability of vascular tissue of interest.

Suitable imaging modalities include computed tomography (CT), magnetic resonance (MR), positron emission tomography (PET), single photon emission tomography (SPECT), ultrasound (US), optical tomography, and/or other imaging modality. Generally, any scanner capable of performing a dynamic contrast-enhanced scan is contemplated herein. For example, perfusion imaging can be performed by CT using an iodine or heavy metallic nanoparticle contrast agents, MR using a gadolinium or iron-oxide contrast agent, PET and SPECT using radiotracers, US using a microbubble contrast agent, optical tomography using a fluorescent agent, etc.

Figure 1:
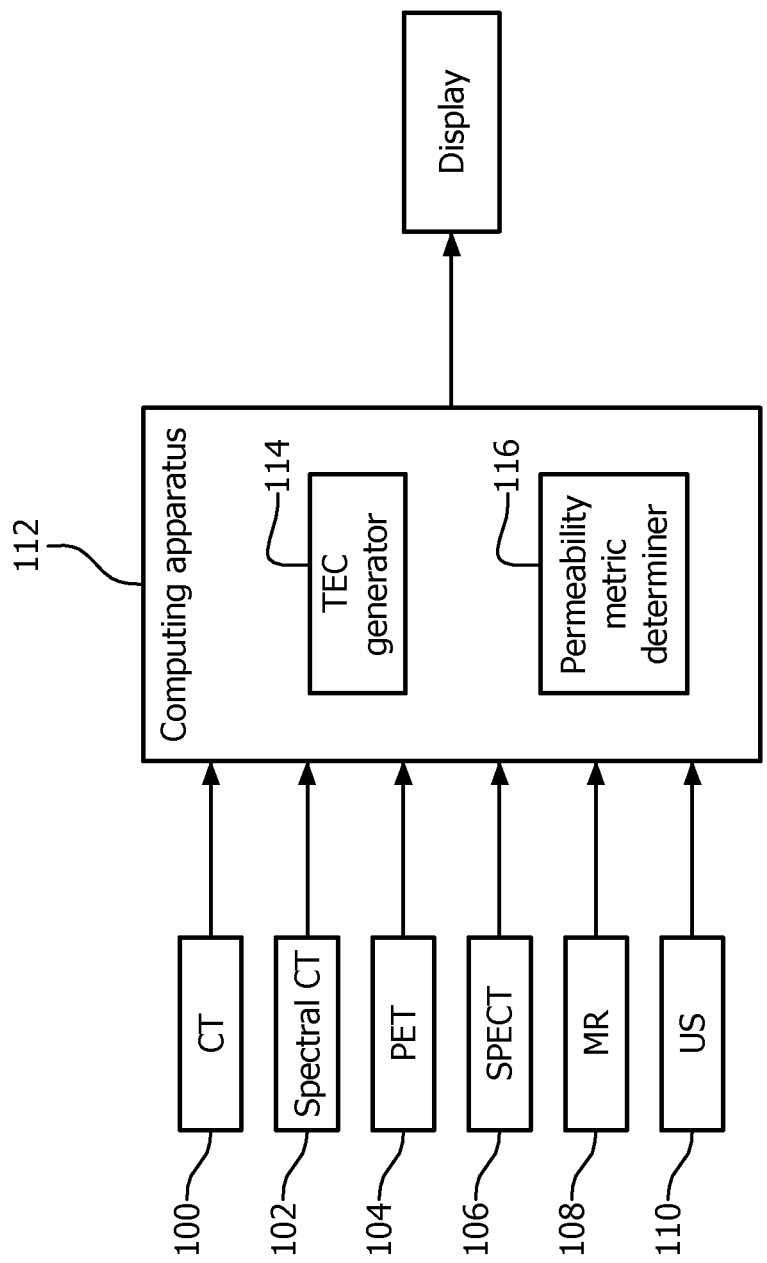

For explanatory purposes and sake of brevity, the following is described in connection with a CT scanner 100, a spectral CT scanner 102, a PET scanner 104, a SPECT scanner 106, a MR scanner 108 and a US scanner 110. Outside of other imaging modalities, it is also to be understood the individual scanners (as shown in FIG. 1) and/or hybrid imaging systems, such as those including multiple modalities like CT/MR, CT/PET, CT/SPECT, PET/MR, etc. are contemplated herein. The scanners 100-110 may be located at a same imaging center or at least one of the scanners 100-110 may be located at a different imaging center.

Turning to FIG. 1, the (conventional) CT scanner 100 includes a generally stationary gantry and a rotating gantry, which is rotatably supported by the stationary gantry and rotates around an examination region about a z-axis. A radiation source, such as an x-ray tube, is rotatably supported by the rotating gantry, rotates with the rotating gantry, and emits radiation that traverses the examination region. A radiation sensitive detector array subtends an angular arc opposite the radiation source across the examination region. The detector array detects radiation traversing the examination region and generates projection data indicative thereof. A reconstructor reconstructs the projection data, generating 3D volumetric image data.

The spectral CT scanner 102 is similar to the conventional CT scanner 100 but includes energy-resolving detector (e.g., photon counting, scintillator/photodiode with at least two detector layers with different spectral sensitivities, etc.) and discrimination hardware and/or software. K-edge spectral imaging leverages the phenomena that high-Z elements tend to attenuate photons to a much higher extent above a particular energy (the K-edge energy of an element) relative to attenuating photons just below the K-edge energy. The discontinuity in the attenuation behavior can be detected using an energy-resolving detector. Other spectral configurations include two or more x-ray tubes that emit radiation with different mean spectrums, an x-ray tube that switches between different emission voltages, etc.

The PET scanner 104 includes a ring of gamma radiation detectors arranged around an examination region. The detectors are configured to detect 511 keV gamma rays indicative of electron-positron decays occurring in an examination region. Most decays result in two 511 keV gamma rays emitted almost 180 degrees to each other, and PET scanners localize the source along a line of response (LOR) there between. The detectors convert the photons into a corresponding electrical signal, and a coincidence event identifier identifies coincident gamma pairs by identifying photons detected in temporal coincidence. The identified pairs are used to generate data indicative of the spatial distribution of the decays.

The SPECT scanner 106 includes a gamma radiation detector and a collimator, which is disposed between an examination region and the gamma radiation detector. The collimator includes radiation attenuating septa that only allow gamma radiation having a certain angle of incidence to reach the gamma detector. Gamma rays are acquired from a number of angles with respect to the examination region by rotating the gamma radiation detector around the examination region. The detector generally is positioned close to the subject under evaluation. A SPECT reconstructor reconstructs the projections to produce volumetric data representative of the distribution of the radioisotope emitting the gamma rays in the object or subject.

The MR scanner 108 includes a main magnet, gradient (x, y, and z) coils, and a RF coil. The main magnet (superconducting, resistive, or permanent) produces a substantially homogeneous, temporally constant main magnetic field $B_0$ in the examination region. The gradient coils generate time varying gradient magnetic fields along the x, y, and z-axes of the examination region. The RF coil produces radio frequency signals (at the Larmor frequency of nuclei of interest (e.g., hydrogen, etc.)) that excite the nuclei of interest in the examination region and receive MR signals emitted by the excited nuclei. A MR data acquisition system processes the MR signals, and a MR reconstructor reconstructs the data and generates MR images.

The US scanner 110 includes a console and a transducer probe which is connected thereto via a cable or the like. The probe includes a one dimensional (1D) or two dimensional (2D) array (linear, curved, etc.) of transducer elements that are configured to transmit ultrasound signals and receive echoes, which are a result of the interaction between the emitted ultrasound signals and the structure in an examination region. The console includes transmit circuitry that generates pulses that actuate transducer elements to transmit ultrasound signals into the examination region. The console also includes receive circuitry that processes received echoes. An image generator processes the data and generates US images.

Again, other imaging modalities are also contemplated herein.

A computing apparatus 112 processes DCE imaging data generated by the imaging scanners 100-110 and/or other scanner(s). The computing apparatus 112 can be a computer or the like, which includes one or more processors executing one or more computer readable instructions encoded, embed, stored, etc. on computer readable storage medium such as physical memory and/or other non-transitory memory. At least one of the computer readable instructions may be carried by a signal, carrier wave and/or other transitory medium. The apparatus 112 includes a human readable output device such as a monitor and an input device such as a keyboard, mouse, etc.

The computing apparatus 112 includes a time enhancement curve (TEC) generator 114 which generates a TEC for a contrast materials based on the received DCE imaging data. FIG. 2 shows an example TEC 202 for a section of a main artery. A y-axis 204 represents an amount of contrast material and an x-axis 206 represents time. A first part 208 of the TEC 202 represents contrast material uptake up to a peak 210 amount and a second part 212 of the curve 202 represents contrast material washout. The approach described herein is based on imaging data corresponding to at least two contrast materials, one with more strongly permeating particles and one with more weakly permeating particles.

In cancerous tissues, particles of the order of less than 30-40 nm in diameter tend to permeate the capillary vessels and enter the interstices (the space between the vessel endothelial cells) relatively rapidly, whereas larger particles on the order of 100-200 nm in diameter tend to slowly permeate the capillary vessels. Contrast materials such as contrast agents and radiotracers are usually constructed from small molecules, e.g., smaller than 20 nm. Larger particles can be constructed by encapsulating several smaller molecules inside a nano-carrier shell made of, e.g., liposomes, polymeric nanoparticles, etc., or by other known techniques.

FIGS. 3 and 4 show examples respectively of smaller and larger particle permeability through a capillary vessel. In FIG. 3, some smaller particles 302 have permeated a vessel 304, entering interstitial tissue 306, while other smaller particles 308 flow through the vessel 304. In FIG. 4, relative to FIG. 3, larger particles 402 have not permeated the vessel 304 and entered interstitial tissue 306. FIG. 5 shows example TECs, including the TEC 202 of FIG. 2, and a TEC 502 of a contrast material with more strongly permeating particles and a TEC 504 of a contrast material with more weakly permeating particles in connection with a tumor.

In FIG. 5, the y-axis 204 represents the amount of contrast material and the x-axis 206 represents time. As shown, the contrast material with more strongly permeating particles (corresponding to TEC 502) has a higher level of contrast material and over a longer period of time, due, e.g., to the accumulation of particles in the interstices. Generally, a difference 506 between the TECs 502 and 504 of the contrast materials with the strongly and weakly permeating particles is indicative of permeability of the tumor and can be used to determine a tissue permeability metric for the tumor.

The computing apparatus 112 further includes a (tissue) permeability metric determiner 116 that determines the permeability metric based on the TECs. EQUATION 2 describes a non-limiting approach for determining the permeability metric:

$$f_{permeability} = \frac{\alpha}{V} = \frac{1}{n} \cdot \sum_{t=t_0}^{t_n} \frac{c_s(t) - c_w(t)}{\int_0^t b(t') \cdot dt}, \quad \text{EQUATION 2}$$

where $C_s$ and $C_w$ are the strongly-permeating and weakly-permeating contrast agent TECs respectively and $t_0$ to $t_n$ are the measurement time samples. The calculation is performed as a mean of the data points. This solution is a result of two equations (where the weakly-permeating agent has a permeability of zero), EQUATION 3 and EQUATION 4:

$$c_w(t) = rBV \cdot b(t) \quad \text{EQUATION 3}$$

and $$c_s(t) = rBV \cdot b(t) + \frac{\alpha}{V} \int_0^t b(t') dt', \quad \text{EQUATION 4}$$

combined to produce EQUATION 5:

$$\frac{\alpha}{V} = \frac{c_s(t) - c_w(t)}{\int_0^t b(t') \cdot dt}. \quad \text{EQUATION 5}$$

An accurate solution can be derived at the time point where the nominator in EQUATION 5 is sufficiently larger than the measurement noise. A more accurate result can be obtained by averaging on measured time points, as shown in EQUATION 2 above.

In this calculation, only one independent parameter—$\alpha/V$—is calculated, and not two unknown parameters as in the standard Patlak analysis, since, in this approach, rBV is not required, even though it can be calculated independently, also with a higher accuracy. The permeability calculation accuracy is higher than in the Patlak analysis since each time point (with its preceding samples) gives a final permeability assessment result, and the averaging on all these results reduces the potential errors.

Also, the time dependent tissue perfusion component (referred to as $rBV \cdot b(t)$ in the Patlak analysis) does not accurately obey this simple multiplication form in most practical cases of delayed blood flow within the tissue. This approximated term is canceled in the approach described herein and therefore the related inaccuracy is reduced. As a result, in general, less sampling points and acquisition time may be sufficient relative to the standard Patlak analysis.

In a more general case, there are two contrast agents (with TECs $C_1$ and $C_2$) with two arbitrary different permeability factors: $\alpha_1$ and $\alpha_2$ respectively, as shown in EQUATION 6:

$$\frac{(\alpha_1 - \alpha_2)}{V} = \frac{1}{n} \cdot \sum_{t=t_0}^{t_n} \frac{c_1(t) - c_2(t)}{\int_0^t b(t') \cdot dt}. \qquad \text{EQUATION 6}$$

The permeability parameter of each agent may be expressed in a first approximation as: $\alpha_1 = k_1 \cdot \alpha_0$ and $\alpha_2 = k_2 \cdot \alpha_0$ where $\alpha_0$ is the physiological permeability parameter depending on the specific tissue only, and $k_1$ and $k_2$ are scaling constants of the two agents that can be known or calibrated in advance (k is within the range [0.0 to 1.0], i.e. 0.0 for very large agent particles and 1.0 for very small agent particles. If $k_1$ and $k_2$ are known, the permeability metric can be solved as shown in EQUATION 7:

$$\alpha_0/V = (\alpha_1 - \alpha_2)/(V \cdot (k_1 - k_2)). \qquad \text{EQUATION 7:}$$

The permeability constant of a specific contrast agent or tracer can be derived by a calibration procedure, e.g., by using a DCE phantom with a dedicated permeability element and a reference test agent with very small particles and hence k=1.0. A reference permeability measurement can give directly the value $\alpha_0$ of the phantom element. Then, by using the specific calibrated agent the parameter $\alpha_1$ can be measured and therefore $k_1$ can be calculated.

In a more general case, if $\alpha_1 = k_1 \cdot \alpha_0$ and $\alpha_2 = k_2 \cdot \alpha_0$, and where $k = F(\alpha_0)$ and F is a known mathematical function, the calibration procedure is also applicable in a similar manner for example using a parameter fitting technique.

The computing apparatus 112 can visually present one or more of the TECs, the permeability metric, and/or the imaging data, individually and/or in combination (e.g., side by side, superimposed, etc.). A range of normal and/or abnormal permeability values may also be displayed along with the permeability metric. In addition, an inferred status and/or recommended course of action can be generated and displayed. The status may indicate a stage, response to treatment, and/or other characteristics about a tumor. The recommended course of action may include another imaging procedure, treatment, etc.

Generally, the permeability metric can be used to grade tumors since increased permeability is associated with immature or damaged blood vessels, which are seen with abnormal neoangiogenesis, study the response of tumors to various therapies, especially antiangiogenic therapy, help in understanding the mechanism of the entry of therapeutic agents into target cells, and hence to improve drug delivery, and/or to gain other information about a tumor. The computing apparatus 112 can also generate a signal indicative thereof and convey the signal to another apparatus.

Figure 6:
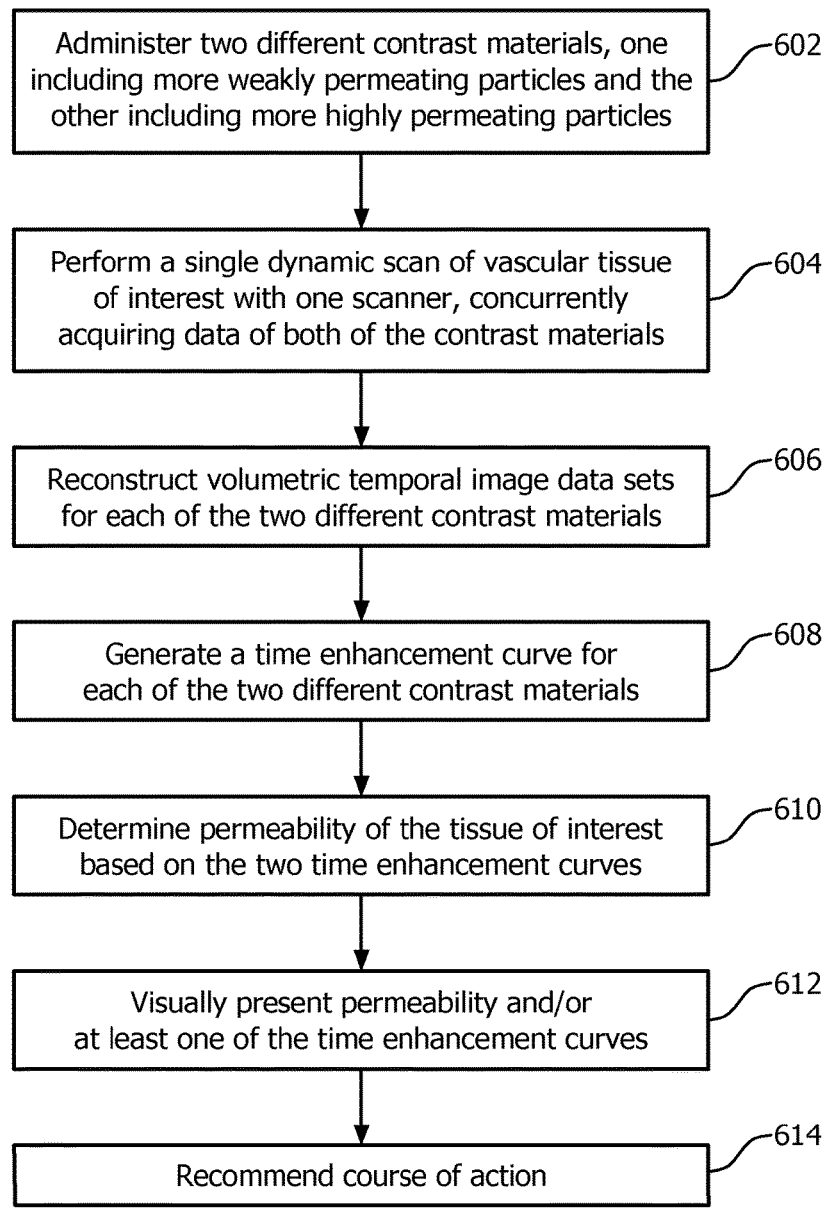
FIG. 6 illustrates an example method for determining a permeability of vascular tissue of interest based on time enhancements curves from image data from a same single scan.
Figure 7:
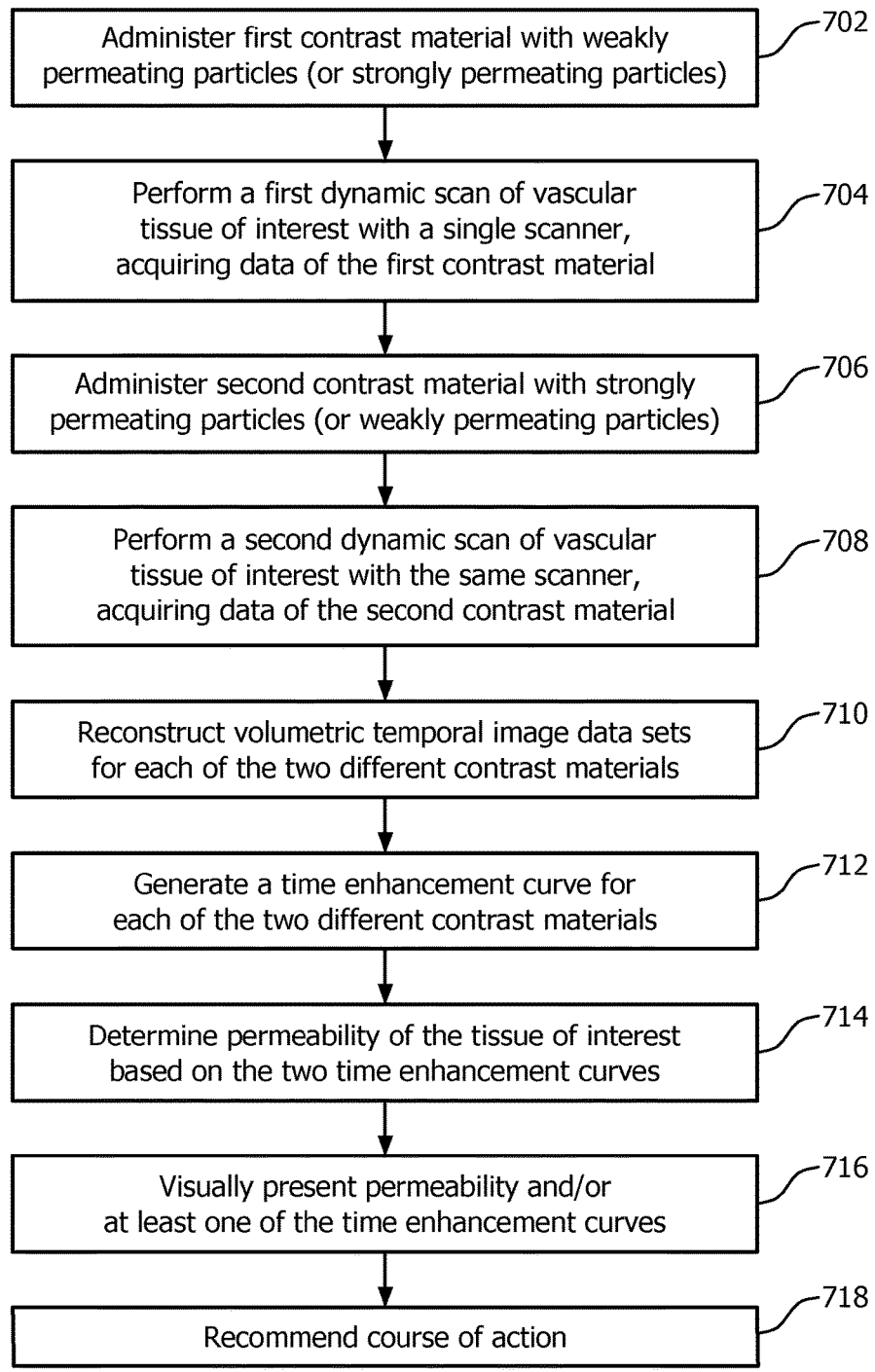
FIG. 7 illustrates an example method for determining a permeability of vascular tissue of interest based on time enhancements curves from image data from different scans but the same single scanner.
Figure 8:
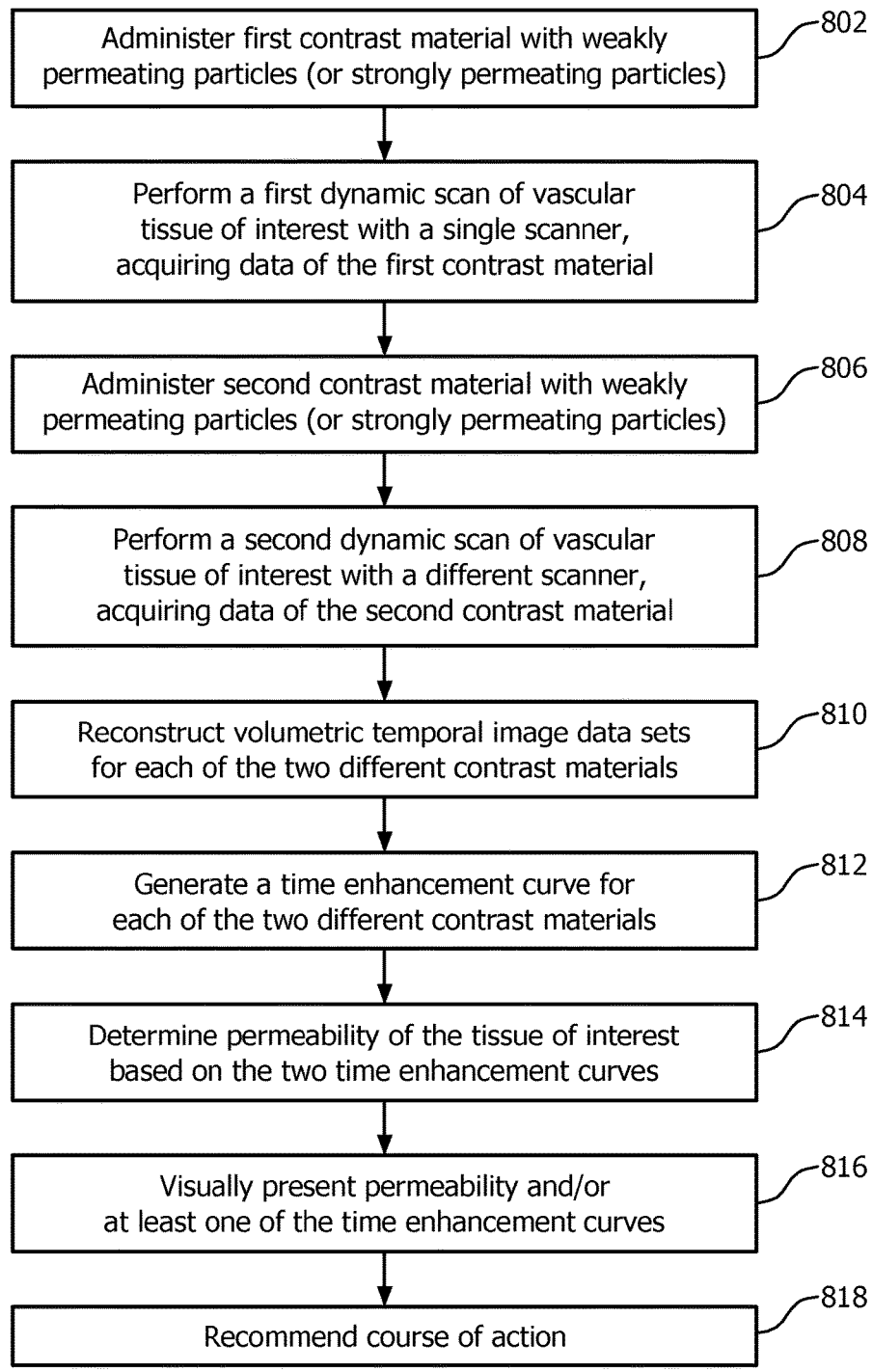
FIG. 8 illustrates an example method for determining a permeability of vascular tissue of interest based on time enhancements curves from image data from different scan performed with different scanner.

FIGS. 6, 7, and 8 illustrate methods for determining permeability of vascular tissue of interest.

It is to be appreciated that the ordering of the acts is not limiting. As such, other orderings are contemplated herein. In addition, one or more acts may be omitted and/or one or more additional acts may be included.

FIG. 6 illustrates a method for determining permeability of vascular tissue of interest concurrently using two different contrast agents and acquiring image data of the contrast agent with a single scan by a single imaging modality.

At 602, two contrast materials, including a first contrast material with weakly permeating particles and a second contrast material with strongly permeating particles, are administered to a subject At 604 a single contrast-enhanced imaging procedure using a single imaging modality is performed, concurrently acquiring data of both the first contrast material and the second contrast material.

At 606, the data is reconstructed, generating volumetric temporal imaging data for each of the two different contrast materials.

At 608, a time enhancement curve is generated for each of the contrast materials based on the corresponding volumetric temporal imaging data.

At 610, a permeability of the vascular tissue of interest is determined based on the two time enhancement curves, and a signal indicative thereof is generated.

At 612, at least one of the two time enhancement curves and/or the permeability metric is visually presented.

At 614, a recommended course of action is determined and visually presented based on at least the permeability metric.

In one instance, the single imaging modality is a spectral CT scanner that can simultaneously identify two different contrast materials based on different k-edge materials and the contrast materials include iodine (k-edge=33.2 keV) and gadolinium (k-edge=50.2 keV), gold (k-edge=80.7 keV) or bismuth (k-edge=90.5 keV), and/or other k-edge materials with k-edge energies in the diagnostic imaging range (e.g., 40 keV to 140 keV).

In another instance, the single imaging modality is a SPECT scanner that can simultaneously identify two different radiotracers and the contrast materials include different radionuclide isotopes such as Tc99m, Tl201, etc. In another instance, the single imaging modality is a MRI scanner that can simultaneously identify two different contrast agents based on different materials and the contrast materials include gadolinium, iron-oxide, etc.

FIG. 7 illustrates a method for determining permeability of vascular tissue of interest sequentially using two different contrast agents and separately acquiring image data of the two contrast agents with two separated scan and a single imaging modality.

At 702, a first contrast material, including either weakly permeating particles or strongly permeating particles, is administered to a subject At 704 a single contrast-enhanced imaging procedure using a single imaging modality is performed, acquiring data of the first contrast material.

At 706, after lapse of a predetermined time delay, a second contrast material, including the other of the weakly permeating particles or the strongly permeating particles, is administered to a subject At 708 a single contrast-enhanced imaging procedure using a single imaging modality is performed, acquiring data of the second contrast material.

Alternatively, the contrast material with the strongly permeating particles is administered first.

At 710, the data is reconstructed, generating volumetric temporal imaging data for each of the two different contrast materials.

At 712, a time enhancement curve is generated for each of the contrast materials based on the corresponding volumetric temporal imaging data.

At 714, a permeability of the vascular tissue of interest is determined based on the two time enhancement curves, and a signal indicative thereof is generated.

At 716, at least one of the two time enhancement curves and/or the permeability metric is visually presented.

At 718, a recommended course of action is determined and visually presented based on at least the permeability metric.

The two different DCE scans are performed with sufficient time delay between them so that the uptake and washout of each contrast agent can be independently discerned. The two different agents can be based on the same material such as iodine for CT, gadolinium for MRI, F-18 for PET, etc. In this option, any conventional imaging system and modality can be used in principle as in a conventional perfusion scan.

FIG. 8 illustrates a method for determining permeability of vascular tissue of interest sequentially using two different contrast agents and separately acquiring image data of the two contrast agents with two separated scan and a two different imaging modalities.

At 802, a first contrast material, including either weakly permeating particles or strongly permeating particles, is administered to a subject.

At 804 a single contrast-enhanced imaging procedure using one imaging modality is performed, acquiring data of the first contrast material.

At 806, a second contrast material, including the other of the weakly permeating particles or the strongly permeating particles, is administered to a subject.

At 808, a single contrast-enhanced imaging procedure using a different imaging modality is performed, acquiring data of the second contrast material.

At 810, the data is reconstructed, generating volumetric temporal imaging data for each of the two different contrast materials.

At 812, a time enhancement curve is generated for each of the contrast materials based on the corresponding volumetric temporal imaging data.

At 814, a permeability of the vascular tissue of interest is determined based on the two time enhancement curves, and a signal indicative thereof is generated.

At 816, at least one of the two time enhancement curves and/or the permeability metric is visually presented.

At 818, a recommended course of action is determined and visually presented based on at least the permeability metric.

The two DCE scans are performed with different modalities and with different contrast agents. The different modalities can be part of the same scanner or two different scanners, which may be at the same imaging center or different imaging centers. For example, the scanner may be a PET/CT hybrid scanner, where the PET DCE scan is performed with a radiotracer and the DCE-CT scan is performed with a contrast material.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

It is to be appreciated that other approaches to distinguishing permeability, other than a size of the molecules, is contemplated herein. For example, characteristics such as hydrophilic nature of molecules, test results for permeability, etc. can additionally or alternatively be used to distinguish permeability.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
determining, with a processor, a permeability metric of a vascular tissue of interest based on a difference between a first time enhancement curve and second time enhancement curve corresponding to a first contrast material and a second contrast material flowing through the vascular tissue of interest, wherein the first and second contrast materials are different; and
generating, with the processor, a signal indicative of the permeability metric, wherein the difference is an average on weighted differences between the first and second time enhancement curves, and the permeability metric is used to automatically determine a tumor grade.

2. The method of claim 1, further comprising:
receiving first dynamic contrast enhanced imaging data and generating the first time enhancement curve based thereon, wherein the first time enhancement curve corresponds to first dynamic contrast enhanced imaging data representing the vascular tissue of interest and a first contrast material; and
receiving second dynamic contrast enhanced imaging data and generating the second time enhancement curve based thereon, and the second time enhancement curve corresponds to second dynamic enhanced imaging data representing the vascular tissue of interest and a second contrast material.

3. The method of claim 1, wherein the first time enhancement curve corresponds to first dynamic contrast enhanced imaging data representing vascular tissue of interest and a first contrast material with more permeable particles, and wherein the second time enhancement curve corresponds to second dynamic contrast enhanced imaging data representing the vascular tissue of interest and a second contrast material with less permeable particles.

4. The method of claim 3, further comprising:
receiving the first dynamic contrast enhanced imaging data and generating the first time enhancement curve based thereon; and receiving the second dynamic contrast enhanced imaging data and generating the second time enhancement curve based thereon.

5. The method of claim 3, wherein the first and second dynamic contrast enhanced imaging data are from a same single contrast enhanced scan.

6. The method of claim 3, wherein the first and second dynamic contrast enhanced imaging data are from different contrast enhanced scans and a same imaging system.

7. The method of claim 1, wherein the first and second dynamic contrast enhanced imaging data are from different contrast enhanced scans and different imaging systems.

8. The method of claim 3, wherein the more permeable particles have a size less than 40 nanometers in diameter, and wherein the less permeable particles have a size between 100 and 200 nanometers in diameter.

9. The method of claim 8, wherein the more permeable particles and the less permeable particles have same size molecules, the less permeable particles have more molecules relative to the more permeable particles, and the less permeable particles include molecules encapsulated inside a nano-carrier shell.

10. The method of claim 1, wherein one of the first contrast material is a contrast agent and the other of the first and second contrast materials is a radiotracer.

11. The method of claim 1, further comprising:
visually presenting the permeability metric.

12. The method of claim 1, further comprising:
determining a state of the vascular tissue of interest based on the permeability metric and visually presenting information representative of the state.

13. The method of claim 1, further comprising:
determining a recommended course of action based on the permeability metric and visually presenting information representative of the state.

14. A computing apparatus, comprising:
a processor configured to receive first dynamic contrast enhanced imaging data representing vascular tissue of interest and a first contrast material with weakly permeating particles and receive second dynamic contrast enhanced imaging data representing the vascular tissue of interest and a second contrast material with strongly permeating particle, and generate first time enhancement curve for the first contrast material and a second time enhancement curve for the second contrast material; and
the processor configured to determine a permeability metric for the vascular tissue of interest by determining a difference between the first and second time enhancement curves, wherein the difference is an average on weighted differences between data points of the first and second time enhancement curves, and the permeability metric is used to automatically determine a tumor grade.

15. The computing system of claim 14, wherein the first and second dynamic contrast enhanced imaging data is from a same single contrast enhanced scan.

16. The computing system of claim 14, wherein the first and second dynamic contrast enhanced imaging data are from different contrast enhanced scans and a same imaging system.

17. The computing system of claim 14, wherein the first and second dynamic contrast enhanced imaging data are from different contrast enhanced scans and different imaging systems.

18. The computing system of claim 14, wherein the more permeable particles have a size less than 40 nanometers in diameter, and wherein the less permeable particles have a size between 100 and 200 nanometers diameter.

19. The computing system of claim 18, wherein the more permeable particles and the less permeable particles have same size molecules, the less permeable particles have more molecules relative to the more permeable particles, and the less permeable particles include molecules encapsulated inside a nano-carrier shell.

20. The computing system of claim 14, wherein the computing system visually presents the permeability metric.

21. The computing system of claim 14, wherein the computing system at least one of determines a state of the vascular tissue of interest based on the permeability metric and visually presenting information representative of the state or determines a recommended course of action based on the permeability metric and visually presenting information representative of the state.

22. A non-transitory computer readable storage medium encoded with one or more computer executable instructions, which, when executed by a processor of a computing system, causes the processor to:
determine a permeability metric of vascular tissue of interest based on a difference between a first time enhancement curve and second time enhancement curve corresponding to a first contrast material and a second contrast material flowing through the vascular tissue of interest, wherein the first and second contrast materials are different, and visually displaying at least one of the permeability metric or the first or second time enhancement curves, wherein the difference is an average on weighted differences between the first and second time enhancement curves, and the permeability metric is used to automatically determine a tumor grade.

* * * * *